(12) United States Patent
Busacca et al.

(10) Patent No.: US 8,519,176 B1
(45) Date of Patent: Aug. 27, 2013

(54) PROCESS FOR PREPARATION OF SUBSTITUTED P-AMINOPHENOL

(75) Inventors: Carl A. Busacca, Poughkeepsie, NY (US); Magnus C. Eriksson, Brookfield, CT (US); Jinghua Xu, Danbury, CT (US); Xingzhong Zeng, New Milford, CT (US)

(73) Assignee: Boehringer Ingelheim International GmbH, Ingelheim Am Rhein (DE)

( * ) Notice: Subject to any disclaimer, the term of this patent is extended or adjusted under 35 U.S.C. 154(b) by 327 days.

(21) Appl. No.: 12/896,602

(22) Filed: Oct. 1, 2010

Related U.S. Application Data

(60) Provisional application No. 61/248,717, filed on Oct. 5, 2009.

(51) Int. Cl.
*C07C 229/22* (2006.01)

(52) U.S. Cl.
USPC .............................................. 560/46; 560/85

(58) Field of Classification Search
USPC ...................................... 560/85, 46
See application file for complete search history.

(56) References Cited

U.S. PATENT DOCUMENTS

| | | | |
|---|---|---|---|
| 8,088,760 B2* | 1/2012 | Chu et al. | 514/210.21 |
| 8,242,140 B2* | 8/2012 | Beaulieu et al. | 514/335 |
| 2010/0280268 A1* | 11/2010 | Dams et al. | 560/13 |
| 2012/0101091 A1* | 4/2012 | Beaulieu et al. | 514/232.8 |
| 2012/0289526 A1* | 11/2012 | Alvaro et al. | 514/274 |

OTHER PUBLICATIONS

Rodrgues et al; Tetrahedron Letters, 46 (2005) 5945-5947.*

* cited by examiner

*Primary Examiner* — Johann R Richter
*Assistant Examiner* — Pancham Bakshi
(74) *Attorney, Agent, or Firm* — Michael P. Morris; David A. Dow

(57) ABSTRACT

The present invention is related to a process of preparing substituted p-aminophenol compound of formula (I) or a salt thereof,

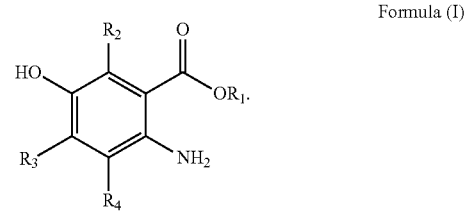

Formula (I)

16 Claims, No Drawings

PROCESS FOR PREPARATION OF SUBSTITUTED P-AMINOPHENOL

CLAIM TO PRIORITY

Priority is hereby claimed to U.S. Provisional Application No. 61/248,717 filed on Oct. 5, 2010.

BACKGROUND OF THE INVENTION

The present invention is related to a process of preparation of a substituted p-aminophenol compound or a salt thereof.

Substituted p-aminophenol is an organic intermediate with extensive applications. It is mainly used in pharmaceutical and dyestuff sectors. In the pharmaceutical sector it can be used in the production of p-acetaminophenol and also in the synthesis of α-p-Chlorophenoxyisobutyrate (CHB), vitamin B1, phenacetin, composite nicotinamide and inhibitors of the hepatitis C Virus polymerase. In the dyestuff sector it is used in the production of azo dyes, direct dyes, sulfur dyes and acid dyes. Besides, p-aminophenol can also be used to synthesize many important intermediates such as p-phenylphenol. The known process of preparation of thep-aminophenol in the art, while suitable for the synthesis of small quantities, is not suitable for large scale manufacture.

There is a continuing need to develop alternative processes of preparation of substituted p-aminophenol with fewer synthetic steps, improved scalability, more efficient isolation and purification of the product, easier handling, better yields, less reaction time, less consumption of starting materials, enhanced safety, reduced contamination to the environment, and reduced costs associated with the process.

SUMMARY OF THE INVENTION

The present invention is related to a process of preparation of a compound of substituted p-aminophenol or a salt thereof. The present process differs from processes disclosed in the prior art, and has both technical and economical advantages over those processes, such as, for example, less expensive, commercially available starting materials; fewer synthetic steps; better yields; improved scalability; easier handling; enhanced safety; reduced contamination of the environment; and more efficient isolation and purification of the product.

DETAILED DESCRIPTION OF THE INVENTION

Definitions and Abbreviations

As used herein, the term "aryl" refers to all-carbon monocyclic, bicyclic, or polycyclic groups of 6 to 12 carbon atoms having a completely conjugated pi-electron system, which may be optionally substituted. Examples of aryl include, but are not limited to: phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, and 2-iodo-4-methylphenyl.

The terms "heteroaryl" refer to a substituted or unsubstituted monocyclic, bicyclic, or polycyclic group of 5 to 12 ring atoms containing one or more ring heteroatoms selected from N, O, and S, the remaining ring atoms being C, and, in addition, having a completely conjugated pi-electron system. Examples of such heteroaryl rings include, but are not limited to, furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The terms "heteroaryl" also include heteroaryl rings with fused carbocyclic ring systems that are partially or fully unsaturated, such as a benzene ring, to form a benzofused heteroaryl. For example, benzimidazole, benzoxazole, benzothiazole, benzofuran, quinoline, isoquinoline, quinoxaline, indole, and the like. Furthermore, the terms "heteroaryl" include fused 5-6, 5-5, 6-6 ring systems, optionally possessing one nitrogen atom at a ring junction. Examples of such hetaryl rings include, but are not limited to, pyrrolopyrimidinyl, imidazo[1,2-a]pyridinyl, imidazo[2,1-b]thiazolyl, imidazo[4,5-b]pyridine, pyrrolo[2,1-f][1,2,4]triazinyl, and the like. Heteroaryl groups may be attached to other groups through their carbon atoms or the heteroatom(s), if applicable. For example, pyrrole may be connected at the nitrogen atom or at any of the carbon atoms.

The term "$(C_1-C_6)$alkyl" includes both branched and straight chain alkyl groups. Typical alkyl groups contemplated by the present invention include methyl, ethyl, n-propyl, isopropyl, n-butyl, sec-butyl, isobutyl, ten-butyl, n-pentyl, isopentyl, n-hexyl, and the like.

Unless otherwise specified, the term "$(C_3-C_{12})$cycloalkyl" refers to a 3-12 carbon mono-cyclic, bicyclic, or polycyclic aliphatic ring structure, optionally substituted with for example, alkyl, hydroxy, oxo, and halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl, and the like.

The term "halo" refers to fluoro, chloro, bromo, or iodo.

The term "salt" refers to salts prepared from chemically or pharmaceutical acceptable non-toxic acids. When a compound of the present invention is basic, its corresponding salt can be conveniently prepared from chemically or pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The term "purification" in the context of purification of product from reaction mixture refers to chromatograph and/or recrystallization.

TABLE 1

| Abbreviations | |
| --- | --- |
| Bn | Benzyl group |
| Boc | tert-butoxycarbonyl |
| br | Broad |
| $CD_3OD$ | Deuterated methanol |
| $CDCl_3$ | Deuterated chloroform |
| d | Doublet |
| DCM | dichloromethane |
| dd | Doublet of doublets |
| DIEA | diisopropylethylamine |
| DMF | N,N-dimethylformamide |
| DMSO | dimethyl sulphoxide |
| ESI | Electrospray Ionization for mass spectrometry |
| $Et_3N$ | triethylamine |
| EtOAc | ethyl acetate |
| EtOH | ethanol |
| HCl | Hydrochloric acid |
| HRMS | High Resolution Mass Spectroscopy (electrospray ionization positive scan) |

TABLE 1-continued

Abbreviations

| | |
|---|---|
| LCMS | Liquid Chromatography - Mass Spectroscopy |
| LRMS | Low Resolution Mass Spectroscopy (electrospray or thermospray ionization positive scan) |
| LRMS (ES⁻) | Low Resolution Mass Spectroscopy (electrospray ionization negative scan) |
| m | Multiplet |
| m/z | Mass spectrum peak |
| MeOH | methanol |
| MHz | Megahertz |
| MS | Mass spectroscopy |
| NaH | Sodium hydride |
| NMM | N-methylmorpholine |
| NMP | 1-methyl-2-pyrrolidinone |
| NMR | Nuclear Magnetic Resonance |
| Pg. | Page |
| q | Quartet |
| Rpm | Revolutions per minute |
| s | Singlet |
| t | Triplet |
| TFA | trifluoroacetic acid |
| THF | Tetrahydrofuran |
| TLC | Thin layer chromatography |
| Vol. | Volume |
| δ | Chemical shift |

One embodiment of the present invention is related to a process of preparing a compound of formula (I) or a salt thereof,

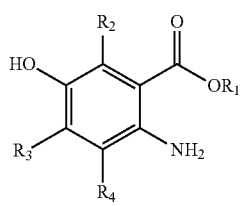

Formula (I)

wherein $R_1$ is ($C_{1-6}$) alkyl, or ($C_{3-12}$)cycloalkyl;

$R_2$, $R_3$, and $R_4$ are each independently selected from H, F, Cl, $CF_3$, CN, —OH, —$NH_2$, ($C_{1-6}$) alkyl, ($C_{3-12}$)cycloalkyl, —NH($C_{1-6}$)alkyl, —NH($C_{3-12}$)cycloalkyl, —N(($C_{1-6}$)alkyl ($C_{3-12}$)cycloalkyl) and —N(($C_{1-6}$)alkyl)$_2$; wherein each of $R_1$ to $R_4$ is optionally substituted by one or more substituents selected from H, F, Cl, $CF_3$, OXO, $CF_3$, CN, ($C_{1-6}$) alkyl, ($C_{3-12}$)cycloalkyl, —OH, —SH, —O($C_{1-6}$) alkyl, —S($C_{1-6}$) alkyl, —$NH_2$, —NH($C_{1-6}$) alkyl, aryl and heteroaryl; comprising:

Step A: converting a compound of formula (II) to a compound of formula (III) according to reaction scheme 1:

Scheme 1

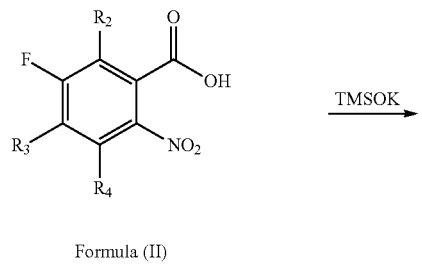

Formula (II)

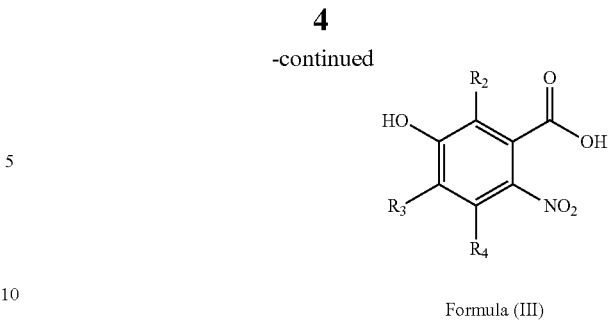

Formula (III)

wherein the compound of Formula (I) is reacted with a suitable amount of potassium trimethylsilanolate (TMSOK) in the presence of a suitable solvent at a suitable reaction temperature for a suitable reaction time to provide the compound of formula WO, wherein said compound of formula (III) is obtained via a suitable isolation procedure; Step B: converting the compound of formula (III) to a compound of formula (IV) according to reaction scheme 2:

Scheme 2

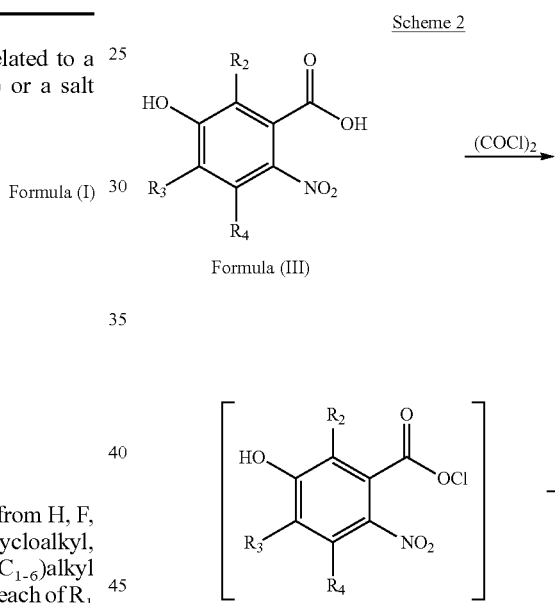

Formula (IV)

wherein the compound of formula (III) is reacted with a suitable amount of oxalyl chloride in the presence of a suitable solvent and at a suitable reaction temperature for a suitable reaction time to form an acid chloride intermediate; and then said acid chloride intermediate is reacted with a suitable amount of alcohol at a suitable reaction temperature for a suitable reaction time to provide the compound of formula (IV), wherein said compound of formula (IV) is obtained via a suitable isolation procedure; and Step C: converting the compound for formula (IV) to a compound of formula (I) according to reaction scheme 3:

Scheme 3

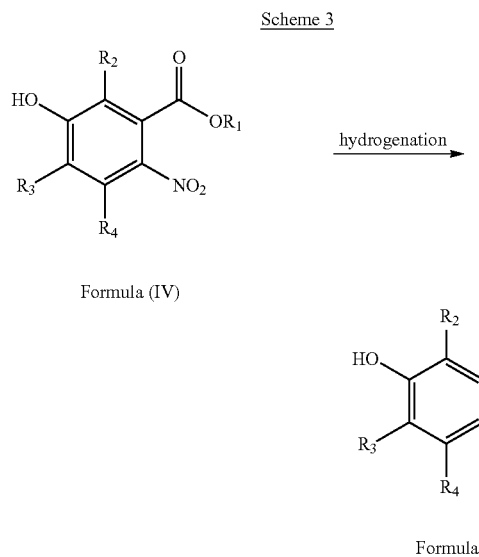

Formula (IV)

Formula (I)

wherein the compound of formula (IV) is hydrogenated in the presence of a suitable amount of a suitable catalyst, a suitable solvent and at a suitable reaction temperature to provide a compound of formula (I), wherein said compound of formula (I) is obtained via a suitable isolation procedure.

In a typical preparation of the compound of formula (III) as described in scheme I, the compound of Formula (II) is reacted with a suitable amount of potassium trimethylsilanolate (TMSOK) in the presence of a suitable solvent at a suitable reaction temperature for a suitable reaction time to provide the compound of formula (III), wherein said compound of formula (III) is obtained via a suitable isolation procedure. Said suitable solvent includes, but is not limited to, dimethylformamide (DMF), dimethylacetamide (DMAc), diethyleneglycol dimethylether (Diglyme), 2-methyltetrahydrofuran (MeTHF), acetonitrile, tetrahydrofuran or mixture of two or more of the solvents. Preferably, the solvent is 2-methyltetrahydrofuran (MeTHF). Said reaction temperature is from 50° C. to 80° C., and preferably from 65° C. to 70° C. Said reaction time is from 2 to 3 hours after addition of the compound of formula (II) into the reaction is complete. Said suitable amount of potassium trimethylsilanolate (TMSOK) is from 3 to 3.5 equivalents compared to the amount of the compound of formula (II). Upon the conversion, the product yield is at least 99.5° A) as analyzed by HPLC, the reaction mixture is cooled to room temperature, then quenches the reaction by adding water, adjusts the pH of the reaction mixture to be acidic, separates the organic layer from the aqueous layer of the reaction mixture, washes the organic layer with water, reduces the volume of organic layer to form a residue of the crude product, stirs the residue of the crude product in a solvent to form a slurry suspension wherein said solvent includes, but is not limited to, Methyl tert-butyl ether (MTBE), hexane, ether, petroleum ether, methanol, benzene, water, ethanol, acetonitrile, tetrahydrofuran, toluene, methylcyclohexane or mixture of two or more of the solvents, preferably a mixture of toluene and methylcyclohexane wherein the volume ratio of toluene and methylcyclohexane is 2:1, filters the slurry suspension, and dries the solid to provide the compound of formula (III). The yield of the compound of formula (III) is at least about 90%, and the compound of formula (III) is obtained on a scale of at least 30 grams without purification. The above-described reaction is preferably carried out at about atmospheric pressure although higher or lower pressures are used if desired.

Another embodiment of the invention relates to a process for Step A wherein the compound of Formula II is reacted with a suitable amount of KOH, or NaOH to provide a compound of Formula III wherein said compound III is obtained via a suitable isolation procedure.

A preferred list of compounds of Formula (III) synthesized according to scheme 1 is selected from the group consisting of:

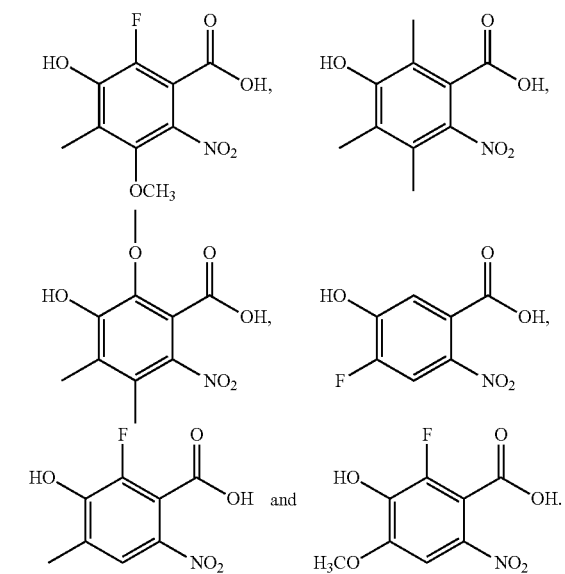

In a typical preparation of the compound of formula (IV) as described in scheme 2, the compound of formula (III) is reacted with a suitable amount of oxalyl chloride in the presence of a suitable solvent and at a suitable reaction temperature for a suitable reaction time to form an acid chloride intermediate; and then said acid chloride intermediate is reacted with a suitable amount of alcohol at a suitable reaction temperature for a suitable reaction time to provide the compound of formula (IV), wherein said compound of formula (IV) is obtained via a suitable isolation procedure. Said suitable solvent includes, but is not limited to, 2-methyltetrahydrofuran (MeTHF), acetonitrile, tetrahydrofuran, toluene or mixture of two or more of the solvents. Preferably, the solvent is 2-methyltetrahydrofuran (MeTHF). Said suitable reaction temperature to form the acid chloride intermediate is from 10° C. to 30° C., preferably 20° C. Said reaction time to form the acid chloride intermediate is from 1 to 2 hours after addition of oxalyl chloride into the reaction is complete. Said suitable amount of oxalyl chloride is from 1 to 1.5 equivalents compared to the amount of the compound of formula preferably 1.25 equivalents compared to the amount of the compound of formula (III). Said alcohol includes, but is not limited to, methanol, ethanol, propanol, butanol, isopropanol, or t-butanol. Preferably the alcohol is anhydrous methanol. Said suitable amount of alcohol is from 5 to 15 equivalents compared to the amount of the compound of formula (III), preferably 10 equivalents compared to the amount of the compound of formula (III). Said suitable reaction temperature to convert the acid chloride intermediate to the compound of formula (IV) is from 10° C. to 30° C., and preferably 20° C. Said reaction time to convert the acid chloride intermediate to the compound of formula (IV) is from 2 to 4 hours after addition of the alcohol into the reaction is complete. Upon the conversion the yield of the product is at least 99.5% pure as analyzed by HPLC, the pH of the reaction mixture is adjusted to be neutral by adding basic reagents into the reaction mixture, then separates the organic layer from the aqueous layer of the reaction mixture, reduces the volume of organic layer to form a residue of the crude product, stirs the residue of the crude product in a solvent to form a slurry suspension wherein said solvent includes, but is not limited to, Methyl tert-butyl ether (MTBE), hexane, ether, petroleum ether, methanol, benzene, water, ethanol, acetonitrile, tetrahydrofuran, toluene, methylcyclohexane or mixture of two or more of the solvents, preferably a mixture of toluene and hexane wherein the volume ratio of toluene and hexane is 2:1, filtering the slurry suspension, and drying the solid to provide the compound of formula (IV). The yield of the compound of formula (IV) is at least about 92%, and the compound of formula (IV) is obtained on a scale of at least 30 grams without purification. The above-described reaction is preferably carried out at about atmospheric pressure although higher or lower pressures are used if desired.

Another embodiment of the invention relates to a process for Step B wherein a compound of formula III is reacted with a suitable amount of sulfuric acid, MeOH to provide a compound of formula IV wherein said compound of formula IV is obtained via a suitable isolation procedure.

A preferred list of compounds of Formula (IV) synthesized according to scheme 2 is selected from the group consisting of:

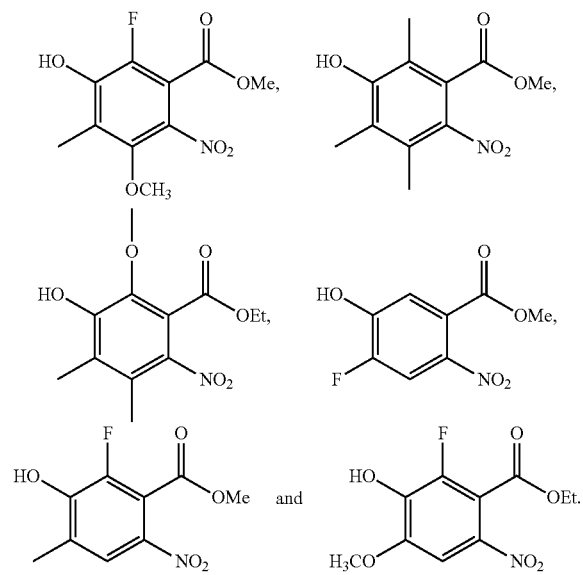

In a typical preparation of the compound of formula (I) as described in scheme 3, the compound of formula (IV) is hydrogenated in the presence of a suitable amount of a suitable catalyst, a suitable solvent and at a suitable reaction temperature to provide a compound of formula (I), wherein said compound of formula (I) is obtained via a suitable isolation procedure. Said suitable solvent includes, but is not limited to, methanol, ethanol, water, acetic acid or mixture of two or more of the solvents, preferably methanol. Said catalyst includes, but is not limited to, palladium on carbon. The preferable catalyst is 5% palladium on carbon. Said suitable amount of the catalyst is from 0.001 to 0.05 equivalent compared to the amount of the compound of formula (IV), preferably 0.005 equivalent compared to the amount of the compound of formula (IV). Said reaction temperature is from 20° C. to 70° C., and preferably is from 20° C. to 25° C. Upon the conversion of the product, the yield is at least 99.5% as analyzed by HPLC, the reaction mixture is diluted with tetrahydrofuran (THF), then filters the resulting mixture through a Celite pad, concentrates the filtrate and dries the filtrate to provide the compound of formula (I). The yield of the compound of formula (I) is at least about 90%, and the compound of formula (I) is obtained on a scale of at least 20 grams without purification.

Another embodiment of the invention relates to a process wherein a compound of formula IV is hydrogenated with palladium on carbon apparatus and then isolated using a suitable isolation procedure.

Another embodiment of the present invention is related to a process of preparation of a salt of the compound of formula (I). In a typical preparation of the salt of the compound of formula (I), a solvent is added into the compound of formula (I) obtained from Step C as described above to form a suspension, then a suitable acid is added into the suspension at a rate where the temperature of the suspension is maintained<below a suitable temperature, and the suspension is stirred at a suitable temperature for a suitable reaction time to provide the salt of the compound of formula (I), wherein said salt of the compound of formula (I) is obtained via a suitable isolation procedure. Said solvent includes, but is not limited to, acetone, acetonitrile, tetrahydrofuran, ethyl acetate or mixture of two or more of the solvents. Preferably, the solvent is ethyl acetate. Said acid comprises acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, or p-toluenesulfonic acid. Preferably, the acid is hydrochloric acid. The temperature of the suspension is maintained below 30° C. during the period of addition of the acid into the suspension. The suitable temperature of stirring the suspension after the completion of the addition of acid is from 20° C. to 50° C., preferably 20° C. Said suitable reaction time is from 1 to 4 hours after addition of the acid into the suspension is complete, preferably 2 hours after addition of the acid into the suspension is complete. The suspension is filtered, and the solid is dried to provide the salt of the compound of formula (I). The yield of the salt of the compound of formula (I) is at least about 90%, and the salt of the compound of formula (I) is obtained on a scale of at least 22 grams without purification.

All processes of preparation, as described above, are supplemented by synthetic methods known in the art of organic chemistry, or modifications and derivatisations that are familiar to those of ordinary skill in the art. The starting materials used herein are commercially available or may be prepared by routine methods known in the art (such as those methods disclosed in standard reference books such as the COMPENDIUM OF ORGANIC SYNTHETIC METHODS, Vol. I-VI (published by Wiley-Interscience)).

During any of the above and/or following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference.

EXAMPLES

The features and advantages of the invention are more fully shown by the following non-limiting examples. These examples illustrate the process of preparation of various compounds of the present invention. Additional compounds within the scope of this invention can be prepared using the methods illustrated in these Examples, either alone or in combination with techniques generally known in the art. As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. Flash chromatography is carried out on silica gel ($SiO_2$) according to the procedure of W. C. Still et al., J. Org. Chem., (1978), 43, 2923.

Reactions were monitored by thin layer chromatography (TLC) and/or HPLC. For the TLC, it was conducted on silica gel 60 $F_{254}$ (0.2 mm) precoated aluminum foil and visualized using UV light. Analytical HPLC is carried out under standard conditions using a Agilent™ Plus C18, 4.6×150 mm, Part Number: 959994-902, 1.8 µM, elution with a mobile phases of 0.2% $H_3PO_4$ and 60 mM $NH_4PF_6$ in HPLC grade water (A) and HPLC grade acetonitrile (B). The flow rate and run time are adjusted to the samples being analyzed. UV detection is at 224 and/or 254 nm. $^1$HNMR (400 MHz or 300 MHz) and $^{13}$C NMR (100.6 MHz) spectra were recorded on Bruker or Varian instruments at ambient temperature with TMS or the residual solvent peak as the internal standard. The line positions or multiples are given in ppm (δ) and the coupling constants (J) are given as absolute values in Hertz (Hz). The multiplicities in $^1$H NMR spectra are abbreviated as follows: s (singlet), d (doublet), t (triplet), q (quartet), quint (quintet), m (multiplet), $m_c$ (centered multiplet), br or broad (broadened), AA'BB'. The signal multiplicities in $^{13}$C NMR spectra were determined using the DEPT135 pulse sequence and are abbreviated as follows: +(CH or $CH_3$), –($CH_2$), $C_{quart}$ (C).

Example 1

Preparation of
2-fluoro-3-hydroxy-4-methyl-6-nitrobenzoic acid

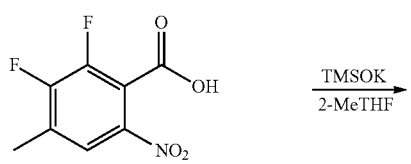
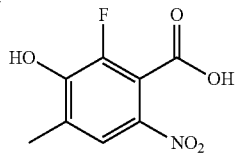

-continued

To a 500 mL glass reactor equipped with mechanical stirrer, addition funnel, thermocouple, reflux condenser and nitrogen inlet is charged potassium trimethylsilanolate (TMSOK, 61.2 g, 0.48 mol, 3.2 eq) and 2-methyl tetrahydrofuran (240 mL) to form a suspension. The suspension is stirred at 20-25° C. 2,3-difluoro-4-methyl-6-nitrobenzoic acid (32.5 g, 0.15 mol, 1 eq) is dissolved in 2-MeTHF (75 mL). To the TMSOK suspension, the solution of 2,3-difluoro-4-methyl-6-nitrobenzoic acid is added. The addition is exothermic and the temperature of the reaction mixture rises to 40-50° C. during addition. After charging is complete, the jacket temperature is set at 65-70° C. The suspension is stirred for 2-3 hour, until HPLC sample shows complete conversion. The mixture is cooled down to room temp. The reaction is quenched with water (100 mL), and acidified to pH 1 with HCl aqueous solution (6M, 90 mL). The layers are separated. The upper organic layer is washed with water (150 mL), and distilled under vacuum to minimum volume. The dark brown residue is stirred in 200 mL of mixed solvent of toluene/methylcyclohexane (v/v, 2:1) to give a suspension. The slurry is filtered. The solid is dried under vacuum to provide the desired product, 2-fluoro-3-hydroxy-4-methyl-6-nitrobenzoic acid (29 g, 90% yield).

Other compounds as contemplated in the present invention can be synthesized via similar preparation procedures as outlined above.

Example 2

Preparation of methyl
5-hydroxy-4-methoxy-2-nitrobenzoate

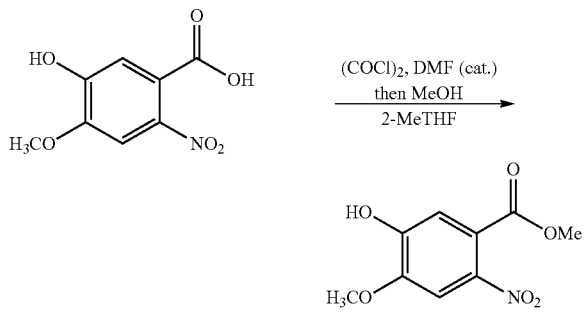

5-hydroxy-4-methoxy-2-nitrobenzoic acid (31.9 g, 0.15 mol, 1.0 eq) and 2-methyltetrahydrofuran (200 mL) are charged into a glass reactor under nitrogen. The solution is stirred and jacket temp is set to 20° C. Oxalyl chloride (24 g, 0.19 mol, 1.25 eq) is added at a rate that the internal temperature is below 25° C. The reaction mixture is stirred for 1-2 hour at 20° C., and cooled to 15° C. Then, anhydrous MeOH (60 ml, 1.5 mol, 10 eq) is added over 15 min, and the reaction temperature is maintained below 25° C. during addition. The reaction mixture is stirred for 2-4 hour at 20° C. until HPLC sample shows complete conversion. $Na_2CO_3$ aqueous solution (1 M, 100 ml) is added to the reaction mixture. Layers are separated. The upper organic layer is distilled under vacuum to minimum volume. The dark brown residue is stirred in 100 mL mixed solvent of toluene/hexane (v/v, 2:1) to give a suspension. The slurry is filtered. The solid is dried under vacuum to provide the desired product, methyl 5-hydroxy-4-methoxy-2-nitrobenzoate (31.3 g, 92% yield).

Other compounds as contemplated in the present invention can be synthesized via similar preparation procedures as outlined above.

Example 3

Preparation of methyl 2-amino-5-hydroxy-3-methylbenzoate hydrochloride

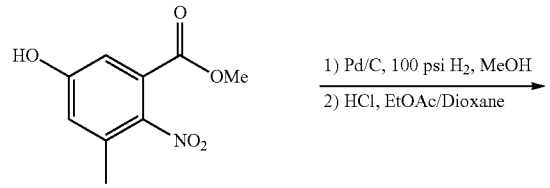

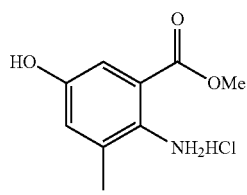

Palladium on carbon (5 wt. %, wet, contains ~50% water, 2.4 g, 0.56 mmol, 0.005 eq) is charged into a 300 mL Parr bomb. Then, methyl 5-hydroxy-3-methyl-2-nitrobenzoate (23.2 g, 0.11 mol, 1 eq) and MeOH (80 mL) are charged. The bomb is sealed, and pressurized/vented three times with hydrogen, and pressured with 100 psi hydrogen. The reaction mixture is stirred, until the hydrogen pressure is not dropping. The bomb is opened, and an HPLC sample shows that the reaction is complete. The mixture is diluted with 80 ml of THF and filtered through a Celite pad. The solution is concentrated under vacuum and solvent is switched to EtOAc. To the suspension in EtOAc (150 mL) at 15° C., HCl in dioxane (4M, 36 mL, 0.14 mol, 1.3 eq) is charged at a rate that the internal temperature is below 30° C. The suspension is stirred at 20° C. for 2 hour. The slurry is filtered. The solid is dried under vacuum to provide the desired product, 2-amino-5-hydroxy-3-methylbenzoate hydrochloride (21.5 g, 90% yield).

Other compounds as contemplated in the present invention can be synthesized via similar preparation procedures as outlined above.

Example 4

Step A:

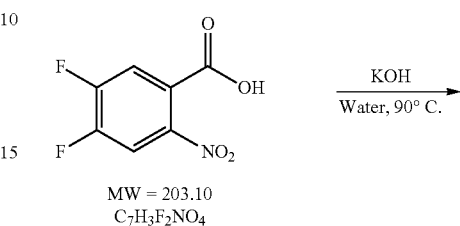

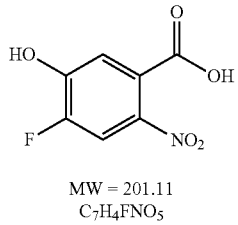

To a 1 L reactor equipped with mechanical stirrer, addition funnel, thermocouple, reflux condenser and nitrogen inlet was charged 4,5-Difluoro-2-nitrobenzoic acid (82 g, 0.4 mol, 1 eq) and water (120 mL) to form a suspension. The suspension was heated to about 50° C. Solution of KOH in water (45 wt. %, 161 g, 1.3 mol, 3.25 eq) was slowly added over about 20 min so that the temperature of the exothermic reaction mixture was kept at 80-90° C. After addition, the mixture was stirred at about 80° C. for about half hour, until HPLC sample showed complete conversion. The mixture was cooled down to room temperature, acidified to pH 1 with concentrated HCl solution (105 ml, 1.26 mol, 3.2 eq), and extracted with 2-methyltetrahydrofuran (630 mL). The layers were separated. The upper organic layer was washed with water (150 mL), and distilled under vacuum to minimum volume. The dark brown residue was stirred in 200 mL of mixed solvent of toluene/methylcyclohexane (v/v, 2:1) to give a suspension. The slurry was filtered. The desired product, 4-fluoro-5-hydroxy-2-nitrobenzoic acid, was obtained as an off-white solid after drying under vacuum (68 g, 85% yield). $^1$H NMR (DMSO-$d_6$, 400 MHz) δ 13.64 (br, 1H), 11.84 (br, 1H), 8.03 (d, J=8.0 Hz, 1H), 7.25 (d, J=12.1 Hz, 1H). $^{13}$C NMR (DMSO-d$_6$, 100 MHz) δ 166.0, 151.6, 150.3, 150.2, 149.1, 138.4, 138.3, 127.0, 117.3, 113.7, 113.5.

Example 5

Step B:

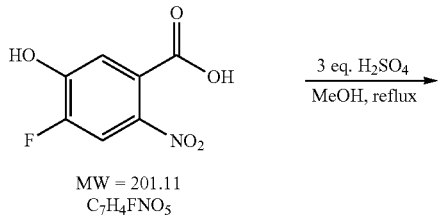

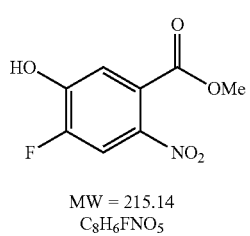

Starting material 4-fluoro-5-hydroxy-2-nitrobenzoic acid, 68 g, 0.34 mol, 1.0 eq) and methanol (140 mL) were charging into a reactor under nitrogen. The solution was cooled to 10-15° C. Sulfuric acid (120 g, 1.2 mol, 3.5 eq) was added at a rate that the internal temperature was below 30° C. The reaction mixture was'refluxed at 65-75° C. for 12-15 hour until HPLC sample showed the conversion was higher than 96%. The mixture was concentrated to minimum volume and the residue was charged into cold water (400 mL) slowly so that the batch was kept below 25° C. The resulting suspension was stirred at 10-15° C. for about 2 hours. The slurry was filtered. The desired product, methyl 4-fluoro-5-hydroxy-2-nitrobenzoate, was obtained as a light brown solid after drying under vacuum (62 g, 85% yield). $^1$H NMR (CDCl$_3$, 400 MHz) δ 7.84 (d, J=9.7 Hz, 1H), 7.25 (d, J=8.4 Hz, 1H), 6.66 (s, 1H), 3.93 (s, 3H). $^{13}$C NMR (DMSO-4, 100 MHz) δ 165.3, 157.6, 151.9, 151.0, 150.8, 149.4, 138.0, 137.9, 125.9, 117.4, 114.1, 113.8, 53.3.

Example 6

Step C:

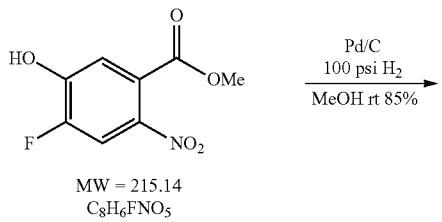

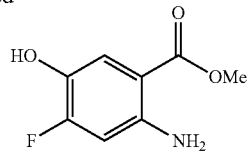

Palladium on carbon (2.5 wt. %, wet, 8.5 g, 0.005 eq) was charged into a 1 L Parr bomb. Then, methyl 4-fluoro-5-hydroxy-2-nitrobenzoate, 62 g, 0.29 mol, 1 eq) and MeOH (300 mL) were charged. The bomb was sealed, and pressurized/vented three times with hydrogen, and pressured with 100 psi hydrogen. The reaction mixture was stirred, until the hydrogen pressure was not dropping. The bomb was opened, and an HPLC sample showed that the reaction was complete. The mixture was diluted with 400 ml of THF and filtered through a Celite pad. The solution was concentrated under vacuum and solvent was switched to MeOH. To the thick suspension in MeOH, water (150 mL) was added in about 30 min. The slurry was filtered. The desired product, methyl 2-amino-4-fluoro-5-hydroxybenzoate, was obtained as off-white solid after drying under vacuum (45.5 g, 85% yield). NMR (DMSO-d$_6$, 400 MHz) δ 9.05 (s, 1H), 7.28 (d, J=10.0 Hz, 1H), 6.54 (d, J=13.4 Hz, 1H), 6.30 (s, 2H), 3.74 (s, 3H). $^{13}$C NMR (DMSO-d$_6$, 100 MHz) δ 167.0, 157.0, 154.5, 146.2, 146.1, 134.5, 134.4, 118.2, 104.7, 103.3, 51.4.

The invention claimed is:

1. A process of preparing a compound of formula (I) or a salt thereof,

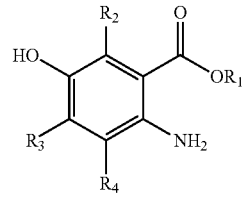

Formula (I)

wherein

R$_1$ is (C$_{1-6}$) alkyl, or (C$_{3-12}$)cycloalkyl;

R$_2$, R$_3$, and R$_4$ are each independently selected from H, F, Cl, CF$_3$, CN, —OH, —NH$_2$, (C$_{1-6}$) alkyl, (C$_{3-12}$)cycloalkyl, —O—(C$_{1-6}$)alkyl, —NH(C$_{1-6}$)alkyl, —NH(C$_{3-12}$)cycloalkyl, (C$_{3-12}$)cycloalkyl) and —N((C$_{1-6}$) alkyl)$_2$; wherein each of R$_1$ to R$_4$ is optionally substituted by one or more substituents selected from H, F, Cl, CF$_3$, OXO, CF$_3$, CN, (C$_{1-4}$ alkyl, (C$_{3-12}$)cycloalkyl, —OH, —SH, —O(C$_{1-6}$) alkyl, —S(C$_{1-6}$) alkyl, —NH$_2$, —NH(C$_{1-6}$) alkyl, aryl and heteroaryl;

comprising:

Step A: converting a compound of formula (II) to a compound of formula (III) according to reaction scheme 1:

Scheme 1

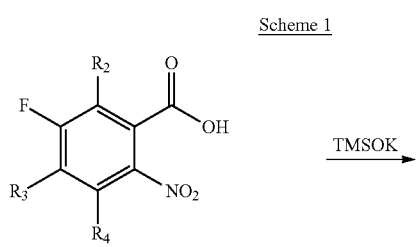

Formula (II)

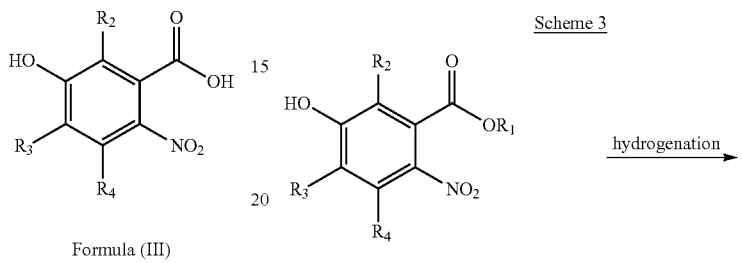

Formula (III)

wherein the compound of Formula (I) is reacted with a suitable amount of potassium trimethylsilanolate (TMSOK) in the presence of a suitable solvent at a suitable reaction temperature for a suitable reaction time to provide the compound of formula (III), wherein said compound of formula (III) is obtained via a suitable isolation procedure;

Step B: converting the compound of formula (III) to a compound of formula (IV) according to reaction scheme 2:

Scheme 2

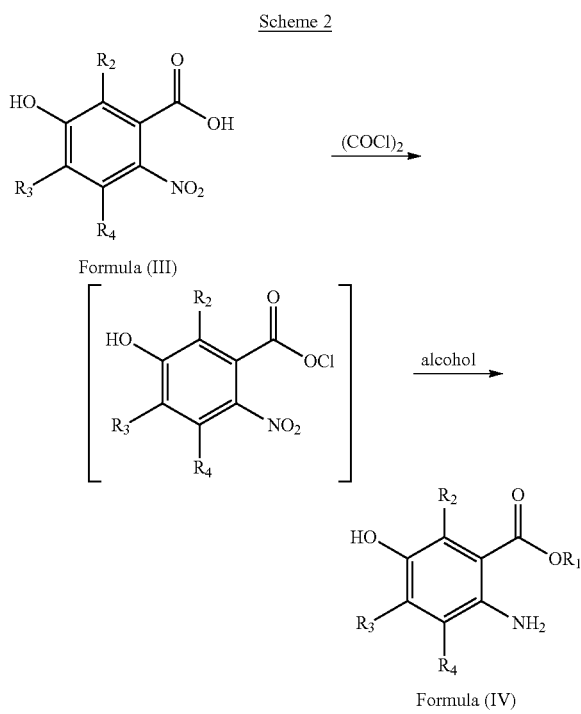

Formula (IV)

wherein the compound of formula (III) is reacted with a suitable amount of oxalyl chloride in the presence of a suitable solvent and at a suitable reaction temperature for a suitable reaction time to form an acid chloride intermediate; and then said acid chloride intermediate is reacted with a suitable amount of alcohol at a suitable reaction temperature for a suitable reaction time to provide the compound of formula (IV), wherein said compound of formula (IV) is obtained via a suitable isolation procedure; and Step C: converting the compound for formula (IV) to a compound of formula (I) according to reaction scheme 3:

Scheme 3

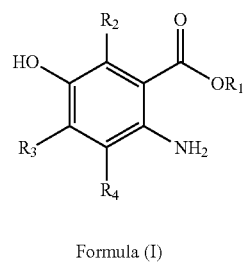

Formula (I)

wherein the compound of formula (IV) is hydrogenated in the presence of a suitable amount of a suitable catalyst, a suitable solvent and at a suitable reaction temperature to provide a compound of formula (I), wherein said compound of formula (I) is obtained via a suitable isolation procedure.

2. The process of claim 1, wherein the suitable solvent in scheme 1 of Step A is 2-methyltetrahydrofuran (MeTHF).

3. The process of claim 1, wherein the isolation procedure of Step A comprise cooling the reaction mixture to room temperature after the reaction is complete, quenching the reaction by adding water, adjusting the pH of the reaction mixture to be acidic, separating the organic layer from the aqueous layer of the reaction mixture, washing the organic layer with water, reducing the volume of organic layer to form a residue of the crude product, stirring the residue of the crude product in a solvent to form a slurry suspension, filtering the slurry suspension, and drying the solid to provide the compound of formula (III).

4. The process of claim 1, wherein the suitable solvent to form the acid chloride intermediate in scheme 2 of Step B is 2-methyltetrahydrofuran (MeTHF).

5. The process of claim 1, wherein the suitable amount of oxalyl chloride in Step B is 1-1.5 equivalents compared to the amount of the compound of formula (III).

6. The process of claim 1, wherein the alcohol of Step B is anhydrous methanol, or ethanol.

7. The process of claim 1, wherein yield of the Step B is at least about 92%.

8. The process of claim 1, wherein the isolation procedure of Step B comprises adjusting the pH of the reaction mixture to be neutral by adding basic reagents into the reaction mixture after the reaction is complete, separating the organic layer from the aqueous layer of the reaction mixture, reducing the volume of organic layer to form a residue of the crude product, stirring the residue of the crude product in a solvent to form a slurry suspension, filtering the slurry suspension, and drying the solid to provide the compound of formula (IV).

9. The process of claim 1, wherein the catalyst of Step C comprises palladium on carbon.

10. The process of claim 1, wherein the solvent of Step C comprises methanol, ethanol, water, acetic acid or mixture of two or more of the solvents.

11. The process of claim 1, wherein the isolation procedure of Step C comprises diluting the reaction mixture with tetrahydrofuran (THF) after the reaction is complete, filtering the resulting mixture through a Celite pad, concentrating the filtrate and drying the filtrate to provide the compound of formula (I).

12. The process of claim 1, wherein the compound of formula (I) is further converted to a salt thereof, comprises adding a solvent to the compound of formula (I) obtained from Step C to form a suspension, adding a suitable acid into the suspension at a rate where the temperature of the suspension is maintained below a suitable temperature, and stirring the suspension at a suitable temperature for a suitable reaction time to provided the salt of the compound of formula (I), wherein said salt of the compound of formula (I) is obtained via a suitable isolation procedure.

13. The process of claim 12, wherein said acid is hydrochloric acid.

14. The process of claim 1, wherein the compound of formula (I) is selected from:

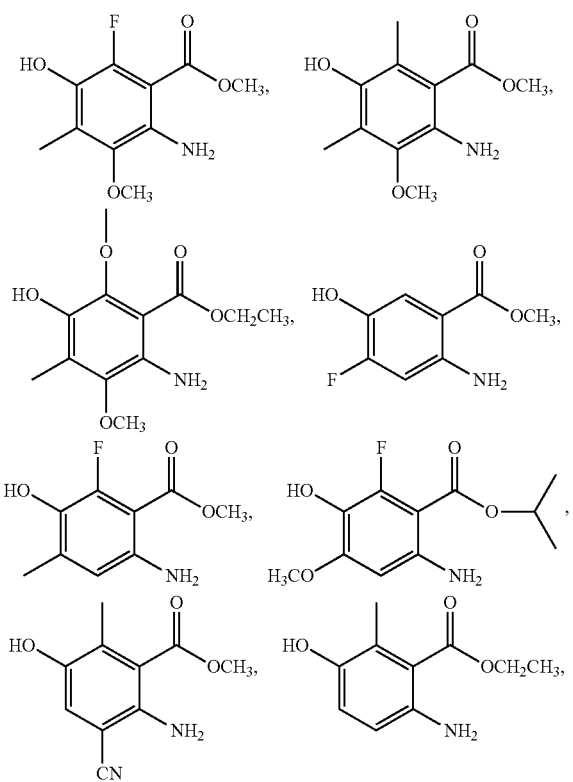

and

15. The process of claim 1, wherein the compound of Formula (III) synthesized according to scheme 1 is selected from the group consisting of:

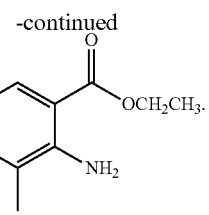

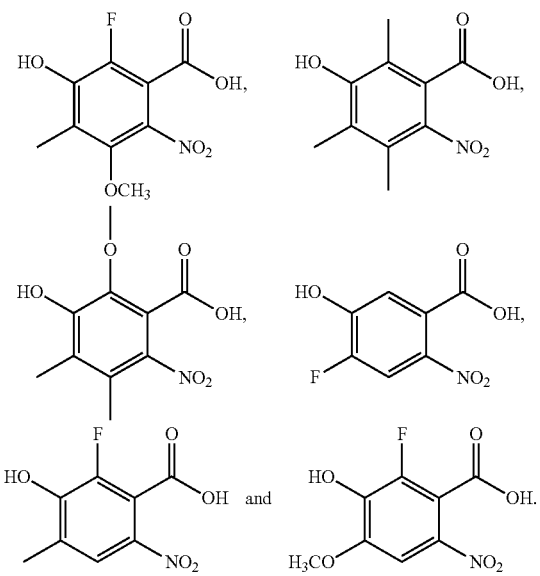

16. The process of claim 1, wherein the compound of Formula (IV) synthesized according to scheme 2 is selected from the group consisting of:

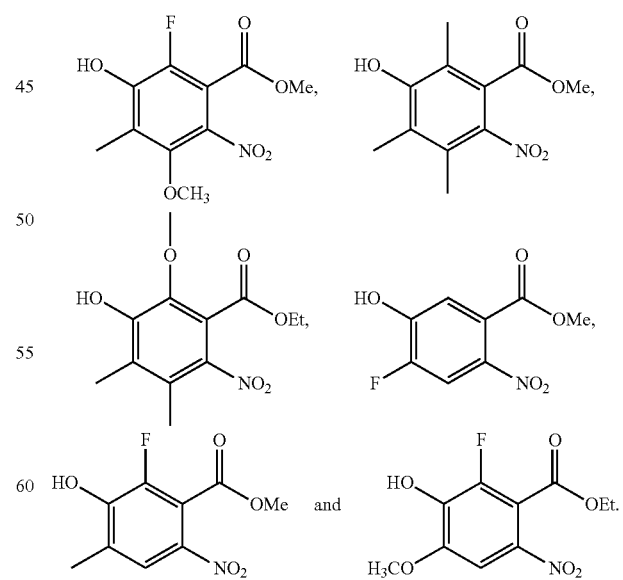

* * * * *